(12) United States Patent
De Tommaso

(10) Patent No.: US 8,268,963 B2
(45) Date of Patent: Sep. 18, 2012

(54) PROCESS FOR THE PURIFICATION OF MACROLIDE ANTIBIOTICS

(75) Inventor: Vincenzo De Tommaso, Monza (IT)

(73) Assignee: Xellia Pharmaceuticals ApS, Copenhagen (DK)

( * ) Notice: Subject to any disclaimer, the term of this patent is extended or adjusted under 35 U.S.C. 154(b) by 668 days.

(21) Appl. No.: 12/095,642

(22) PCT Filed: Dec. 7, 2006

(86) PCT No.: PCT/EP2006/069414
§ 371 (c)(1),
(2), (4) Date: Nov. 11, 2008

(87) PCT Pub. No.: WO2007/068644
PCT Pub. Date: Jun. 21, 2007

(65) Prior Publication Data
US 2010/0228005 A1    Sep. 9, 2010

(30) Foreign Application Priority Data

Dec. 16, 2005   (EP) ..................................... 05112283

(51) Int. Cl.
*C07K 1/34*   (2006.01)
(52) U.S. Cl. ....................................... 530/344; 530/322
(58) Field of Classification Search .................. None
See application file for complete search history.

(56) References Cited

U.S. PATENT DOCUMENTS

| 4,042,575 A | 8/1977 | Eustache |
| 5,223,413 A | 6/1993 | Nagy et al. |
| 5,258,495 A | 11/1993 | Chu |
| 5,853,720 A * | 12/1998 | Pflaum et al. ................. 424/124 |
| 7,192,743 B2 | 3/2007 | Youn et al. |
| 7,405,267 B2 | 7/2008 | Kang et al. |
| 2005/0024581 A1* | 2/2005 | Kim et al. ........................ 514/54 |
| 2005/0245481 A1* | 11/2005 | Youn et al. ........................ 514/54 |

FOREIGN PATENT DOCUMENTS

| CN | 1554773 A | 12/2004 |
| JP | 11080022 | 3/1999 |
| WO | WO 2006/061166 | 6/2006 |

* cited by examiner

*Primary Examiner* — Christopher R. Tate
*Assistant Examiner* — Roy Teller
(74) *Attorney, Agent, or Firm* — Saliwanchik, Lloyd & Eisenschenk

(57) ABSTRACT

The present invention concerns a process for the purification of macrolide antibiotics. More specifically it concerns a process for the purification of macrolide antibiotics that result in a white powder. The powder remains white also after some time of storage. The process of the present invention is performed by dissolving the macrolide antibiotics, e.g. commercial vancomycin hydrochloride, in water and subjecting the solution to ultrafiltration with a membrane having nominal retention lower than 30,000 Da, preferably of 10,000 Da. The purified solution is preferably concentrated by reversed osmosis and then lyophilized at the optimized conditions of pressure and temperature to obtain a white powder.

22 Claims, No Drawings

PROCESS FOR THE PURIFICATION OF MACROLIDE ANTIBIOTICS

CROSS-REFERENCE TO RELATED APPLICATION

This application is the U.S. national stage application of International Patent Application No. PCT/EP2006/069414, filed Dec. 7, 2006, the disclosure of which is hereby incorporated by reference in its entirety.

The present invention concerns a process for the purification of macrolide antibiotics. More specifically it concerns a process for the purification of macrolide antibiotics that result in a white powder. The powder remains white also after some time of storage.

Macrolide antibiotics have macrocyclic lactone chemical structures, which are lactone rings of 12-22 carbon atoms to which sugars can be attached. They are bacteriostatic and bind with ribosomes from bacteria to prevent the production of proteins.

Macrolide antibiotics comprise vancomycin, teicoplanin, erythromycin, azithromycin, clarithromycin, roxithromycin, josamycin, ristocetin, actinoidin, avoparcin, actaplanin, teichomycin and telithromycin.

The present invention is directed to the purification of macrolide antibiotics in general and more particularly to the purification of vancomycin.

U.S. Pat. No. 5,853,720 discloses a process for the purification of vancomycin wherein the purification step makes use of preparative chromatography on a silica gel column.

EP 132 117 discloses a process for the purification of vancomycin class antibiotics making use of affinity chromatography, wherein the antibiotic is bound to a matrix by formation of a sorption complex.

These methods based on chromatography produce an antibiotic with increased purity, but do not produce a powder with satisfactory white colour. In the case of vancomycin, after chromatographic purification, the initial colour is light pink, and after some time, the colour becomes brownish. This is not in line with the requirements of European Pharmacopoeia.

It has been found that, by subjecting the macrolide antibiotic to ultrafiltration it is possible to remove impurities that result in high absorption at 450 nm.

Ultrafiltration is a process for the separation of molecules of different size. The molecular weight of the molecule plays, in fact, the most important role in ultrafiltration, although other secondary factors, such as shape and electric charge of the molecule, can play a role. Commercially, there are available different ultrafiltration membranes, defined by the molecular weight of the molecules that are retained by the membrane. Membranes that are useful in the present invention have retention value lower than 30,000 Da.

The process of the present invention is performed by dissolving the macrolide antibiotics, e.g. commercial vancomycin hydrochloride, in water and subjecting the solution to ultrafiltration with a membrane having nominal retention lower than 30,000 Da, preferably equal to or lower than 15,000 Da, most preferably equal to or lower than 10,000 Da. Preferably, the ultrafiltration membrane has a nominal retention higher than 6,000 Da. The purified solution is preferably concentrated by reversed osmosis and then lyophilized at the optimized conditions of pressure and temperature to obtain a white powder. When it is intended to obtain a sterile powder, it is preferable to pass the solution, after concentration with reverse osmosis, through a 0.22 micron filter and collect the filtrate in a sterile vessel (Class A according to European GMP).

The type of membrane depends on the antibiotic. In the case of vancomycin, by using a membrane having retention value of 30.000 Da, vancomycin passes the membrane, while the impurities remains in the retentate. On the contrary, purification of teicoplanin proved to be effective when using a 10,000 Da membrane. In this case the impurities are in the permeate and teicoplanin is in the retentate. Thus, for each antibiotic it is possible to optimize the type of membrane to achieve optimal separation between impurities and macrolide antibiotic.

When the antibiotic is vancomycin, it is characterized by an absorption at 450 nm lower than 0.100, preferably lower than 0.080.

The macrolide antibiotic is dissolved in water and the concentration of the antibiotic in the starting solution is comprised between 0.1 and 30% by weight, preferably between 1 and 20% by weight, most preferably between 3 and 18% by weight.

EXAMPLES

Vancomycin hydrochloride used in the examples is ca commercial product obtained from Alpharma.

Measures of absorbance at 450 nm were made according to Vancomycin monography of the European Pharmacopoeia.

Example 1

Purification of vancomycin hydrochloride 65 g of commercial vancomycin hydrochloride from Alpharma were dissolved in 500 ml of distilled water. After complete dissolution of the powder, the solution is subjected to ultrafiltration with a 10,000 Da membrane, maintaining a pressure drop of 1 bar between the permeate and the retentate, while the transmembrane pressure drop is 2.5 bar. The permeate is concentrated via reverse osmosis, passed through a 0.22 micron filter and collected in a Class A vessel according to European GMP.

Example 2

Purification of Vancomycin Hydrochloride 30 g of commercial vancomycin hydrochloride from Alpharma were dissolved in 500 ml of distilled water. After complete solubilization, the solution is subjected to ultrafiltration with a 10,000 Da membrane, maintaining a pressure drop of 1 bar between the permeate and the retentate, while the transmembrane pressure drop is 2.5 bar. The permeate is concentrate via reverse osmosis, passed through a 0.22 micron filter and collected in a Class A vessel according to European GMP.

|  | Starting Vancomycin | Example 1 | Example 2 |
|---|---|---|---|
| Absorption at 450 nm | 0.184 | 0.064 | 0.045 |

Example 3

Purification of Teicoplanin 10 g of teicoplanin were dissolved in 100 ml of distilled water. After complete solubilization, the solution is subjected to ultrafiltration with a 10,000 Da membrane, maintaining a pressure drop of 1 bar between the permeate and the retentate, while the transmembrane pressure drop is 2.5 bar. In this case, teicoplanin remains in the retentate, while some impurities pass in the permeate. The retentate is then lyophilised optimizing the conditions of temperature and vacuum, passed through a 0.22 micron filter and collected in a Class A vessel according to European GMP.

Title of teicoplanin measured by HPLC was 89.7% before and 93.8% after purification. The most important impurity was 10.8% before and 6.1% after purification, while a second impurity present before purification with 2.9% totally disappeared after purification.

The invention claimed is:

1. A process of removing color impurities from a powder form of vancomycin comprising:
    dissolving the powder form of vancomycin in water; and
    subjecting the water solution of vancomycin to ultrafiltration with a membrane having nominal retention lower than 30,000 Da; whereby color impurities of the vancomycin are removed.

2. The process according to claim 1 wherein the membrane has nominal retention equal to or lower than 10,000 Da.

3. The process according to claim 1 wherein, after ultrafiltration, the purified solution is lyophilized at the optimized conditions of pressure and temperature to obtain a white powder.

4. The process according to claim 2 wherein, after ultrafiltration, the purified solution is lyophilized at the optimized conditions of pressure and temperature to obtain a white powder.

5. The process according to claim 3 wherein the final powder has absorption at 450 nm lower than 0.100.

6. The process according to claim 4 wherein the final powder has absorption at 450 nm lower than 0.100.

7. The process according to claim 3 wherein the final powder has absorption at 450 nm lower than 0.080.

8. The process according to claim 4 wherein the final powder has absorption at 450 nm lower than 0.080.

9. The process according to claim 3, wherein before lyophilization, the purified solution is concentrated by reverse osmosis.

10. The process according to claim 4, wherein before lyophilization, the purified solution is concentrated by reverse osmosis.

11. The process of claim 1, wherein the powder form of vancomycin to be dissolved in water is of commercial grade.

12. The process of claim 1, wherein the powder form of vancomycin to be dissolved in water contains light pinkish and/or brownish color impurities.

13. The process of claim 1, wherein the powder form of vancomycin to be dissolved in water has absorption at 450 nm of about 0.184 or higher.

14. A process of removing color impurities from powder form a of vancomycin, wherein the method consists of:
    dissolving the powder form of vancomycin in water;
    removing color impurities of vancomycin by subjecting the water solution of vancomycin to ultrafiltration with a membrane having nominal retention lower than 30,000 Da to obtain a purified vancomycin solution; and, optionally,
    concentrating and/or lyophilizing the purified vancomycin solution to obtain a white powder.

15. The process of claim 14, wherein the membrane has nominal retention equal to or lower than 10,000 Da.

16. The process of claim 14, wherein after ultrafiltration the purified solution is lyophilized at the optimized conditions of pressure and temperature to obtain a white powder.

17. The process of claim 16, wherein before lyophilization the purified solution is concentrated by reverse osmosis.

18. The process of claim 14, wherein the powder form of vancomycin to be dissolved in water is of commercial grade.

19. The process of claim 14, wherein the powder form of vancomycin to be dissolved in water contains light pinkish and/or brownish color impurities.

20. The process of claim 14, wherein the powder form of vancomycin to be dissolved in water has absorption at 450 nm of about 0.184 or higher.

21. The process according to claim 14, wherein the obtained white powder has absorption at 450 nm lower than 0.100.

22. The process according to claim 14, wherein the obtained white powder has absorption at 450 nm lower than 0.080.

* * * * *